(12) United States Patent
Nikou et al.

(10) Patent No.: US 10,864,045 B2
(45) Date of Patent: Dec. 15, 2020

(54) SYSTEMS AND METHODS FOR MEASURING BONE JOINT LAXITY

(71) Applicant: Smith & Nephew, Inc., Memphis, TN (US)

(72) Inventors: Constantinos Nikou, Monroeville, PA (US); Branislav Jaramaz, Pittsburgh, PA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 16/751,888

(22) Filed: Jan. 24, 2020

(65) Prior Publication Data
US 2020/0155237 A1 May 21, 2020

Related U.S. Application Data

(63) Continuation of application No. 16/493,188, filed as application No. PCT/US2018/022456 on Mar. 14, 2018.
(Continued)

(51) Int. Cl.
*A61B 34/10* (2016.01)
*A61B 34/20* (2016.01)
(Continued)

(52) U.S. Cl.
CPC ............ *A61B 34/10* (2016.02); *A61B 5/4504* (2013.01); *A61B 5/4528* (2013.01); *A61B 34/20* (2016.02);
(Continued)

(58) Field of Classification Search
CPC ..... A61B 5/4504; A61B 5/4528; A61B 34/10; A61B 2034/104; A61B 2034/105;
(Continued)

(56) References Cited

U.S. PATENT DOCUMENTS

| 4,913,163 A | * | 4/1990 | Roger | ................. A61B 5/4533 600/595 |
| 6,757,582 B2 | | 6/2004 | Brisson et al. | |
| (Continued) | | | | |

FOREIGN PATENT DOCUMENTS

WO     2017218928 A1     12/2017

OTHER PUBLICATIONS

International Search Report and Written Opinion for PCT/US2018/022456 dated Jun. 18, 2018.

*Primary Examiner* — Larry E Waggle, Jr.
(74) *Attorney, Agent, or Firm* — Troutman Pepper Hamilton Sanders LLP (57) ABSTRACT

A system and device (110) for determining bone laxity. For example, the system includes a tracked probe (300) comprising at least one probe marker (310) and a computer assisted surgical (CAS) system (100). The CAS system includes a navigation system (130) and a processing device (110) operably connected to the navigation system and a computer readable medium configured to store one or more instructions that, when executed, cause the processing device to receive location information from the navigation system, generate (820) a surgical plan comprising a post-operative laxity assumption (720), collect (850) first motion information related to movement of the joint through a first range of motion, collect (860) second motion information related to movement of the joint through a second range of motion, determine (870) a post-operative laxity (710), and compare the post-operative laxity and the post-operative laxity assumption to determine laxity results.

23 Claims, 7 Drawing Sheets

Related U.S. Application Data

(60) Provisional application No. 62/417,286, filed on Mar. 14, 2017.

(51) Int. Cl.
*A61B 5/00* (2006.01)
*A61F 2/46* (2006.01)

(52) U.S. Cl.
CPC .......... *A61F 2/4657* (2013.01); *A61F 2/4684* (2013.01); *A61B 2034/104* (2016.02); *A61B 2034/105* (2016.02); *A61B 2034/108* (2016.02); *A61B 2034/2048* (2016.02); *A61B 2034/2057* (2016.02); *A61B 2034/2068* (2016.02)

(58) Field of Classification Search
CPC .............. A61B 2034/108; A61B 34/20; A61B 2034/2055; A61B 2034/2068; A61F 2/38; A61F 2/4657; A61F 2/4684
See application file for complete search history.

(56) References Cited

U.S. PATENT DOCUMENTS

| | | |
|---|---|---|
| 2007/0219561 A1 | 9/2007 | Lavallee et al. |
| 2008/0319448 A1 | 12/2008 | Lavallee et al. |
| 2010/0010506 A1 | 1/2010 | Murphy |
| 2014/0324403 A1* | 10/2014 | Gotte .................... A61F 2/4657 703/2 |
| 2016/0228193 A1 | 8/2016 | Moctezuma et al. |
| 2016/0278754 A1* | 9/2016 | Todorov ............... A61B 17/025 |

\* cited by examiner

FIG. 10

SYSTEMS AND METHODS FOR MEASURING BONE JOINT LAXITY

CLAIM OF PRIORITY

This application is a continuation of U.S. patent application Ser. No. 16/493,188, titled "Systems and Methods for Measuring Bone Joint Laxity," filed Sep. 11, 2019, which is a U.S. national stage filing under 35 U.S.C. § 371 of International PCT Application No. PCT/US2018/022456, filed Mar. 14, 2018, which claims the benefit of priority to U.S. Provisional Application No. 62/471,286, titled "Systems and Methods for Measuring Bone Joint Laxity," filed Mar. 14, 2017, each of which is incorporated herein by reference in its entirety.

TECHNICAL FIELD

The present disclosure relates generally to apparatus, methods, and systems for computer-aided orthopedic surgery. More specifically, the present disclosure relates to computer-aided measurement of joint laxity during a joint replacement procedure.

BACKGROUND

The use of computers, robotics, and imaging to aid orthopedic surgery is known in the art. There has been a great deal of study and development of computer-aided navigation and robotic systems used to both plan for and guide surgical procedures involving joints. In knee replacement surgery, for example, a surgeon develops a plan to place a first implant in the distal end of the patient's femur and a second implant in the proximal end of the tibia. It is important for the implants to be placed in a way that preserves proper alignment of the joint.

Another important consideration when developing a successful surgical plan is the "laxity" within the joint, which refers to the amount of space that exists between the bones in the joint when it is subjected to maximal stresses. Surgeons use this information as a rule of thumb to evaluate the proper maximal tension in the ligaments of the joint. Typically, laxity is measured by pulling the components of the joint with some amount of distraction force to create a "stressed" condition under which data, such as bone spacing and distance, is collected. The distance between the bones in the "stressed" condition is called the "laxity."

It is known to use spacing gauges to measure the laxity, although this technique is inconvenient and possibly difficult depending on the amount of access the surgeon has to the joint space. Some surgeons will instead "eyeball" or estimate the distance based upon a visual inspection, but this can lead to errors depending on the experience of the surgeon in estimating gap widths. Still other surgeons palpate the gap in order to come to some approximation of the laxity, but again, this carries inherent sources of error.

It is also known, in some Computer Aided Surgery systems such as the Navio® system, to use the system to allow for recording of bone positions during "stressed" collection. NAVIO is a registered trademark of BLUE BELT TECHNOLOGIES, INC. of Pittsburgh, Pa. This stressed collection is used to optimize planned positions for implants so that the optimal laxity is theoretically maintained. The implants are then placed in the surgical plan in optimal locations relative to their intended bone surfaces. However, without determining the exact location of the final implant positions, it is hard to know if the planned laxity is actually achieved. What is needed is a method that can be used to measure the actual laxity of the post-operative joint without needing to register the positions of the implants.

SUMMARY

There is provided a system for determining bone laxity during a surgical procedure to replace at least a portion of a bone joint with an implant. The system includes a tracked probe comprising at least one probe marker, the tracked probe configured to provide an indication of at least one anatomical landmark on a bone during the surgical procedure; and a computer assisted surgical system (CAS). The CAS includes a navigation system configured to track the tracked probe and at least one bone marker during the surgical procedure and a processing device operably connected to the navigation system and a computer readable medium. The computer readable medium is configured to store one or more instructions that, when executed, cause the processing device to receive location information related to a position of the tracked probe and the at least one bone marker from the navigation system, generate a surgical plan comprising a post-operative laxity assumption, collect first motion information related to movement of the joint through a first range of motion, collect second motion information related to movement of the joint through a second range of motion, determine a post-operative laxity for the joint, compare the post-operative laxity for the joint and the post-operative laxity assumption to determine laxity results for the surgical procedure, and cause the laxity results to be displayed on a display operably connected to the processing device.

In some embodiments of the system, the first motion information includes baseline information collected while the joint is moved through the first range of motion wherein a first portion of the joint is touching a second portion of the joint. In some additional embodiments, the first portion of the joint is a tibial implant and the second portion of the joint is a femoral implant.

In some embodiments of the system, the second motion information includes distracted motion information collected while the joint is moved through a second range of motion wherein the first portion of the joint is in a distracted position from the second portion of the joint.

In some embodiments of the system, determining the post-operative laxity for the joint comprises determining spatial differences in the first motion data and the second motion data for the at least one bone marker.

In some embodiments of the system, determining the laxity results includes plotting distance information associated with the post-operative laxity assumption to obtain a first laxity curve, plotting distance information associated with the post-operative laxity to obtain a second laxity curve, and comparing the first laxity curve and the second laxity curve.

In some embodiments of the system, the computer readable medium is configured to store one or more additional instructions that, when executed, cause the processing device to update the surgical plan based upon the laxity results.

In some embodiments of the system, the post-operative laxity assumption is based upon implant size information, preservation of an original joint line for the joint, and ensuring sufficient space in the joint for full range of motion. In some additional embodiments, the sufficient space in the joint for full range of motion is determined based upon standard gap information for the joint.

In some embodiments of the system, the joint is a knee.

In some embodiments of the system, the at least one bone marker includes an optical navigation marker mounted on a patient's tibia.

There is also provided a device for determining bone laxity during a surgical procedure to replace at least a portion of a bone joint with an implant. The device includes a processing device operably connected to a navigation system and a computer readable medium. The computer readable medium is configured to store one or more instructions that, when executed, cause the processing device to receive location information related to a position of the tracked probe and the at least one bone marker from the navigation system, generate a surgical plan comprising a post-operative laxity assumption, track movement of the joint through a first range of motion and collect first motion information related to movement of the joint through the first range of motion, track movement of the joint through a second range of motion and collect second motion information related to movement of the joint through the second range of motion, determine a post-operative laxity for the joint, compare the post-operative laxity for the joint and the post-operative laxity assumption to determine laxity results for the surgical procedure, and cause the laxity results to be displayed on a display operably connected to the processing device.

In some embodiments of the device, the first motion information includes baseline information collected while the joint is moved through the first range of motion wherein a first portion of the joint is touching a second portion of the joint. In some additional embodiments, the first portion of the joint is a tibial implant and the second portion of the joint is a femoral implant.

In some embodiments of the device, the second motion information includes distracted motion information collected while the joint is moved through the second range of motion wherein the first portion of the joint is in a distracted position from the second portion of the joint.

In some embodiments of the device, determining the post-operative laxity for the joint comprises determining spatial differences in the first motion data and the second motion data for the at least one bone marker.

In some embodiments of the device, determining the laxity results includes plotting distance information associated with the post-operative laxity assumption to obtain a first laxity curve, plotting distance information associated with the post-operative laxity to obtain a second laxity curve, and comparing the first laxity curve and the second laxity curve.

In some embodiments of the device, the computer readable medium is configured to store one or more additional instructions that, when executed, cause the processing device to update the surgical plan based upon the laxity results.

In some embodiments of the device, the post-operative laxity assumption is based upon implant size information, preservation of an original joint line for the joint, and ensuring sufficient space in the joint for full range of motion. In some additional embodiments, the sufficient space in the joint for full range of motion is determined based upon standard gap information for the joint.

In some embodiments of the device, the joint is a knee.

In some embodiments of the device, the at least one bone marker includes an optical navigation marker mounted on a patient's tibia.

The example embodiments as described above can provide various advantages over prior techniques. For example, the techniques as taught herein can reduce the error associated with existing methods of determining bone laxity during an implant procedure. The techniques also provide for a process to determine bone laxity that can be efficiently integrated into existing surgical procedures using a surgical navigation system.

Further features and advantages of at least some of the embodiments of the present disclosure, as well as the structure and operation of various embodiments of the present disclosure, are described in detail below with reference to the accompanying drawings.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings.

DETAILED DESCRIPTION

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

This disclosure describes example systems and methods of implementing a navigation system to facilitate post-implant laxity determination in an operative joint. In the following description, for purposes of explanation, numerous specific details are set forth in order to provide a thorough understanding of example embodiments. It will be evident to one skilled in the art, however, that embodiments can be practiced without these specific details.

For the purposes of this specification, the term "implant" is used to refer to a prosthetic device or structure manufactured to replace or enhance a biological structure. Additionally, however, the term "implant" could also be used to refer to a trial component that is used mainly for sizing prior to installing a permanent prosthetic device or structure. For example, in a knee replacement procedure, an implant can be placed on one or both of the tibia and femur. While the term "implant" is generally considered to denote a man-made structure (as contrasted with a transplant), for the purposes of this specification, an implant can include a biological tissue or material transplanted to replace or enhance a biological structure.

The navigation system employed in certain embodiments of the present disclosure can track a patient's operative bones throughout a full range of motion as well as a drilling device to align and/or guide the drilling device in cutting the bones to receive implants in a manner consistent with a surgical plan. More specifically, the navigation system not only can be configured to assist the surgeon in planning and performing a surgical procedure such as a joint replacement, but also can be configured to verify that the implants are installed in a manner consistent with the plan.

In certain embodiments, the navigation system can be used in the planning stages of the surgery. Where it is desirable to maintain the same laxity in the joint post-operatively as existed prior to the surgery, the surgeon may employ imageless registration of the involved bones by touching sufficient points on the bones with a tracked probe to register them in the system so they can be tracked. In certain embodiments, the surgeon may stress the joint and track its relative location throughout a full range of motion to determine the pre-operative laxity profile that becomes a goal for the post-operative condition. In certain other embodiments, it may be desirable to employ a standardized gap in the surgical plan. In still other embodiments, a statistical average gap is used in the surgical plan.

Figure 1:
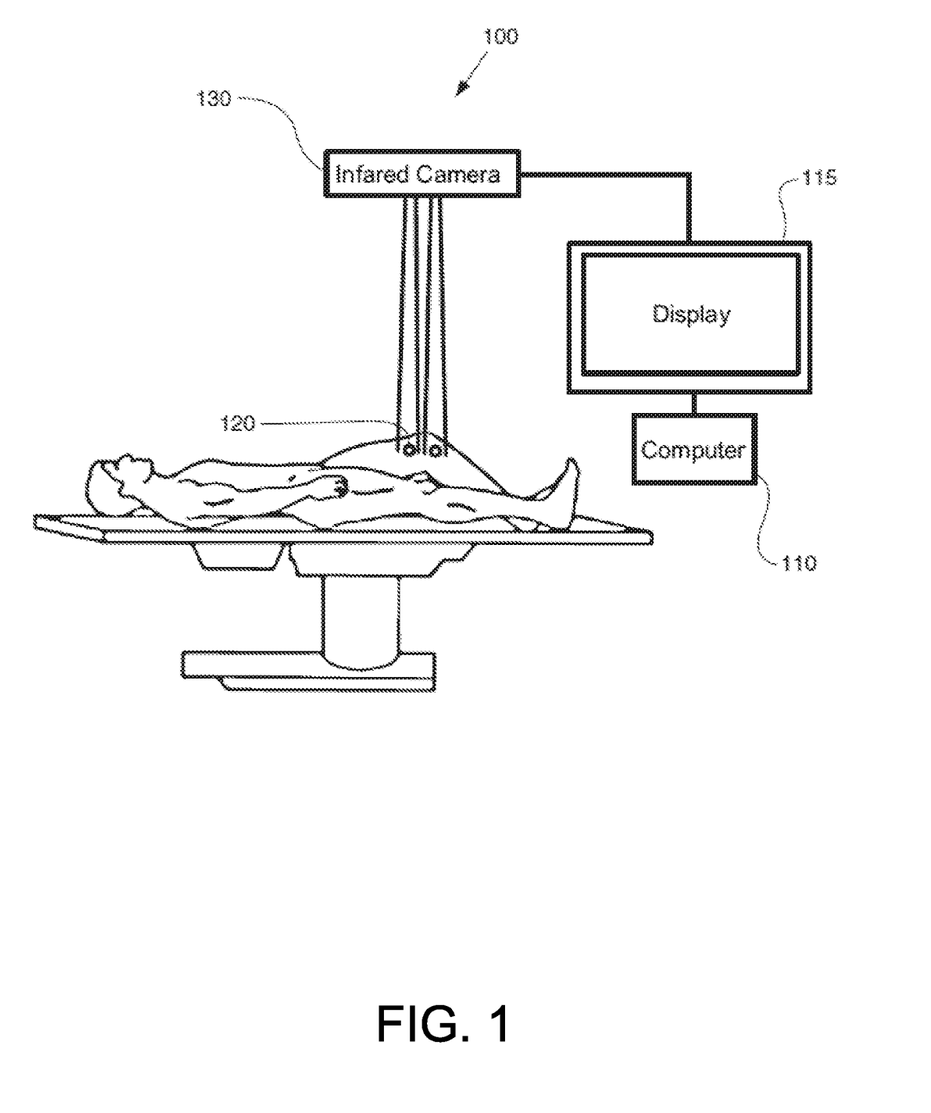
FIG. 1 depicts a block diagram depicting a system for providing surgical navigation to ensure an orthopedic procedure is consistent with a surgical plan, in accordance with certain embodiments of the invention.

FIG. 1 illustrates a block diagram for certain embodiments of a surgical system 100, which includes a computer system 110 that provides a display 115 for viewing location data provided by optical trackers 120 as read by an infrared camera system 130. In certain implementations, the computer 110 can include various components such as a processing device and a computer readable medium configured to store one or more instructions that, when executed, cause the processing device to perform one or more tasks. For example, the instructions can be configured to cause the processing device to calculate bone laxity and determine bone laxity results for a surgical procedure as discussed, for example, in reference to FIG. 10 below.

The optical trackers 120 and infrared camera system 130 can provide data indicating the precise location of the bones in the knee joint at any given time. In certain embodiments, the infrared camera system 130 can detect tracking spheres located on the optical trackers 120 in order to gather location data regarding the patient's femur and tibia on which a knee replacement procedure is to be performed. It is to be appreciated that embodiments of the described subject matter can be implemented by various types of operating environments, computer networks, platforms, frameworks, computer architectures, and/or computing devices.

In certain implementations, various components as shown in FIG. 1 can be arranged into a subsystem of surgical system 100. For example, the infrared camera system 120 and the computer 110 can be configured to function as a surgical navigation system working in concert with additional components of surgical system 100.

Figure 2:
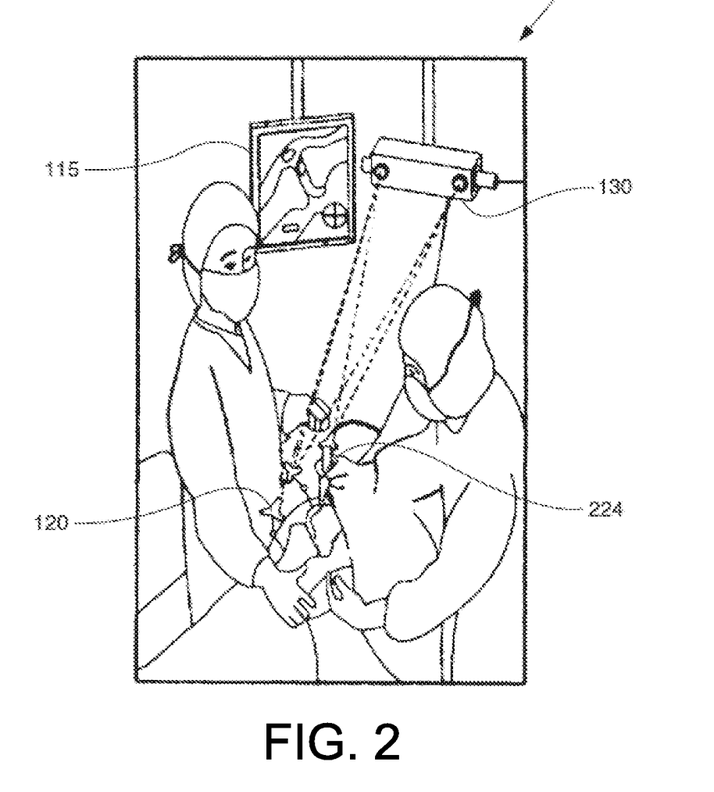
FIG. 2 depicts an illustration of an operating room with a system employing surgical navigation and a cutting tool, in accordance with certain embodiments of the invention.

FIG. 2 illustrates an embodiment of an optical surgical navigation system such as a navigation system integrated into surgical system 100 as described above. The infrared camera system 130 and trackers 120 can be used to perform surgical navigation as discussed. The trackers 120 can be optical trackers and can be rigidly attached to any object (such as the patient's bone and one or more surgical tools or instruments) that the surgeon wishes to track during the procedure. The camera system 130 can be positioned and configured to continuously monitor the surgical workspace for the location of the trackers 120 during the procedure. Using the previously calculated spatial relationship of the trackers 120 to the patient's bones, the position of a first bone of a joint to a second bone in a three-dimensional space can be tracked and continuously output to the display 115. The display 115 can also continuously display a surgical tool 224 (such as a cutting element or probe) location relative to the patient's anatomy. In certain implementations, a computing device such as computer 110 as shown in FIG. 1 can also be configured to continually collect and record location information as tracked by the camera system 130 for further review and/or analysis.

As noted above, in certain embodiments, the surgical system 100 can also include one or more processors and memory devices, as well as various input devices, output devices, communication interfaces, and/or other types of devices. The computer system 110 as described herein can include a combination of hardware and software.

Figure 3:
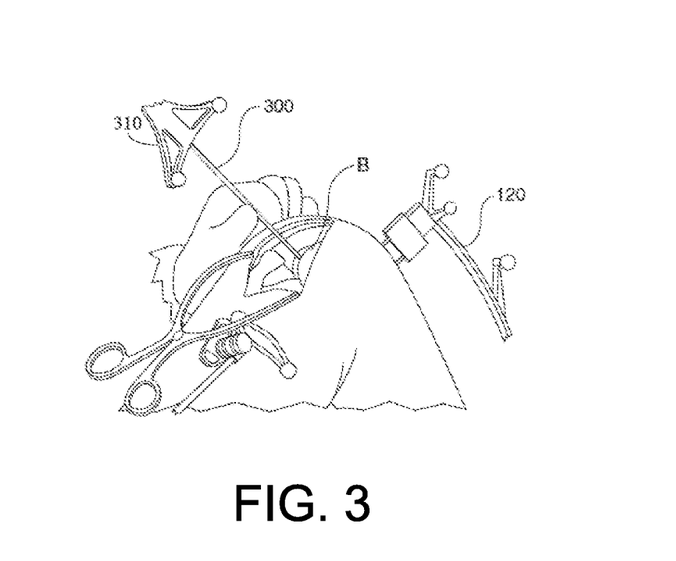
FIG. 3 depicts a close-up illustration of a point probe touching a target bone of a tracked joint, in accordance with certain embodiments of the invention.

FIG. 3 illustrates a tracked probe 300 that can be used in conjunction with certain embodiments. As previously disclosed in U.S. Pat. No. 6,757,582 to Brisson et al., the entirety of which is incorporated herein as if more fully set forth, a tracker array 310 mounted on the tracked probe 300 can be tracked by a camera (such as camera 115 in FIG. 2). The camera can detect, for example, the trackers 120 and the tracker array 310 and communicate that information to a computer system 110. Based upon this information, the computer system 110 can also track the bones, tracked probe 300, and any other tracked items, such as surgical tools, within the surgical space and compare the location of the tracked items with a surgical plan stored on the computer system 110.

It should be noted that, while the presently disclosed method and system can be used for multiple joints and surgical procedures, it will be discussed in relation to a partial knee replacement (UKR) procedure. Those of skill in the art will readily recognize that the method and system could readily be adapted to address a total knee replacement (TKR) procedure, as well as other joint replacement procedures. For example, the techniques as described herein can be adapted for use in an elbow replacement procedure, a shoulder replacement procedure, an ankle replacement procedure, a hip replacement procedure, and other similar joint replacement procedures.

In the process of preparing for a joint replacement procedure, the surgeon or a member of the surgical team creates a surgical plan that identifies what portion of the bones are to be cut so that implants can be installed. This plan takes into account, for example, the selection of certain sized implants, preservation of the original joint line, and ensuring there is sufficient space in the post-operative joint for the full range of motion.

In certain implementations, a critical part of this calculation can include a planned or assumed post-operative laxity for the joint. If the implants are too close together after the procedure, for example, the implants may collide during flexion. Such a result will be suboptimal for the patient due to potential loss of range of motion as well as pain when one or more of the bones are pushed out of their natural position by the other bone in the joint. For example, if the patient tries to perform a certain physical activity such as squatting, the improper laxity may result in limited motion and/or pain associated with contact between the bones in the knee. If, on the other hand, the implants are spaced too far apart post-operatively, there is an increased chance of instability in the joint and potential ligament damage resulting from normal joint usage by the patient.

Using the techniques as described herein, after the bone preparation portion of the procedure has been completed and "trial" implants have been installed, the surgeon has a chance to determine how close the laxity of the post-operative joint matches the laxity goal or assumption used in the surgical plan. The surgical navigation system used in the procedure can be leveraged for this purpose because the exact locations of the bones in the surgical space are being tracked.

Figure 4:
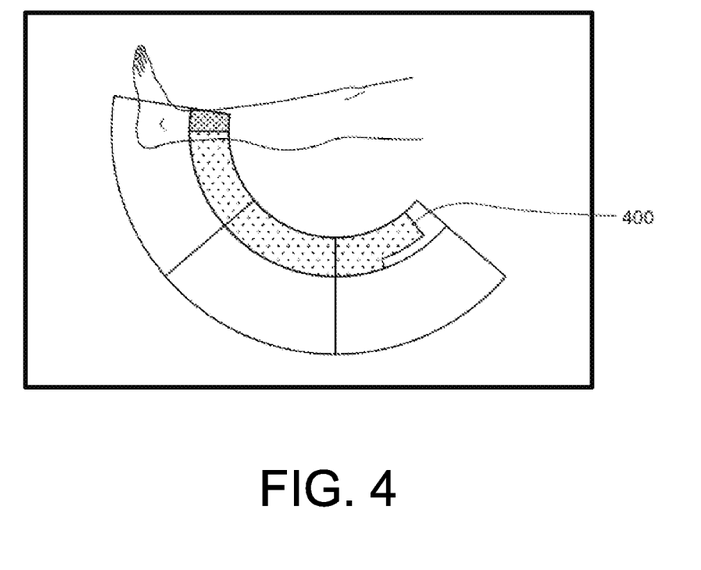
FIG. 4 depicts an illustration of a system display showing a tracked joint through a range of motion, in accordance with certain embodiments of the invention.
Figure 5:
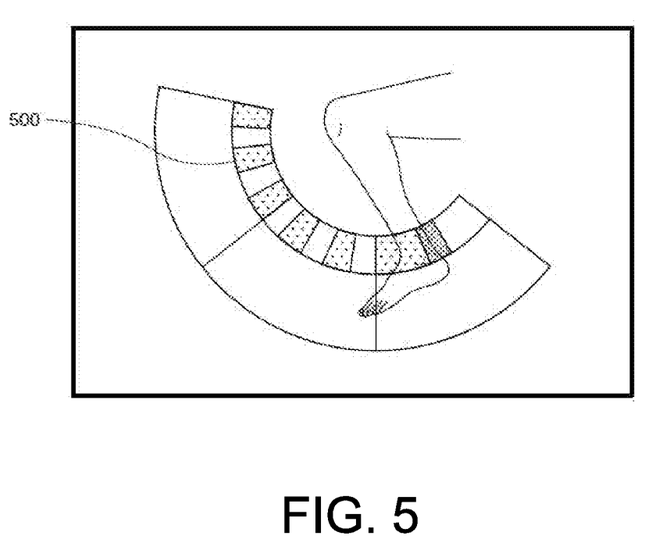
FIG. 5 depicts an illustration of a system display showing a tracked joint through a range of motion, in accordance with certain embodiments of the invention.

In certain embodiments, the process for determining how well the post-operative laxity compares to the laxity goal or assumption involves first placing the joint in a position where the trial implants are touching which, in the case of knee replacement, involves pushing the lower portion of the leg toward the upper portion to force the trial implants to touch. As illustrated in FIGS. 4 and 5, the relative locations of the bones are then collected by the surgical system 100 as the surgeon collects data with the trial implants touching through a full range of motion of the joint. This data set is called the baseline position.

For example, as shown in FIG. 4, an initial curve 400 can be generated including an estimation of the relative position of the bone during the full range of motion. As the leg is moved through the full range of motion of the joint, the actual location of the bone can be tracked and recorded. As shown in FIG. 5, an updated curve 500 can include, for example, information related to the tracked and measured position of the bone throughout the full range of motion of the joint. In certain implementations, the baseline position data set can be determined based upon the updated curve 500.

The next step in the process involves pulling apart or "distracting" the joint until the ligaments are at full, but unforced, stretch. To the extent that pre-operative distracted measurements are taken as part of generating the surgical plan or are otherwise used as a goal for post-operative laxity, it is important that the surgeon distract the lower extremity with approximately the same force for both measurements.

Figure 6:
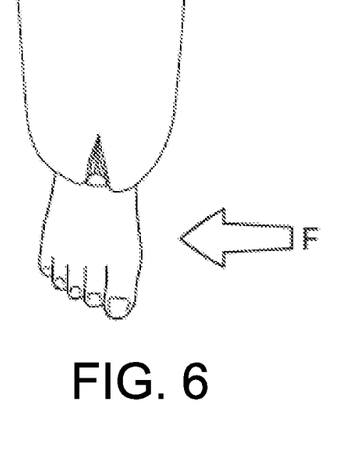
FIG. 6 depicts an illustration of an intended distraction force on an operative joint, in accordance with certain embodiments of the invention.
Figure 7:
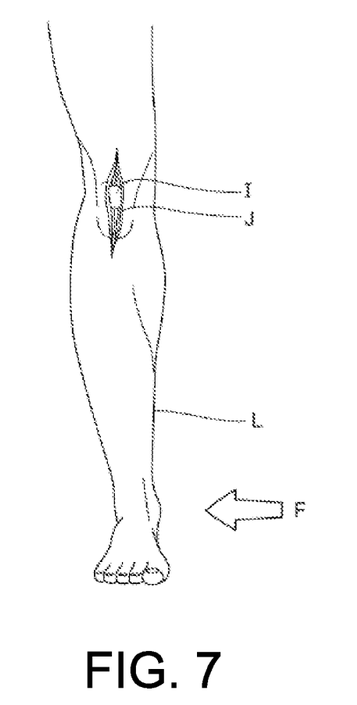
FIG. 7 depicts an illustration of an intended distraction force on an operative joint, in accordance with certain embodiments of the invention.

With reference to FIGS. 6 and 7, a medial UKR procedure has been performed on a patient's right knee and the surgical team distracts the joint by applying a force (F) to the lower extremity (L) containing the patient's tibia J and collecting data throughout a full range of motion. The relative positions of the femur I and tibia J, are collected and compared to the positions of the bones when they were touching in the baseline position (as shown in FIGS. 4 and 5). The difference in the tibial position (relative to the femur) between the baseline position and the distracted position can be calculated. Since the point of interest where the laxity should be measured (i.e. at the implant-to-implant interface) is known, the distance that the tibial point of interest moved between the baseline and distracted positions can be calculated as the actual joint laxity.

In certain embodiments, the laxity can also be measured by identifying the location of a specific point of reference or anatomical landmark on the tibial implant with a tracked point probe, such as tracked probe 300 illustrated in FIG. 3. The location of this point of reference in relation to the trackers in the tibia is fixed. In certain embodiments, the point of reference could be the center point on the articular surface of the tibial implant trial. Location data regarding the relative positions of the bones can then be collected, as described, both with the implants touching (baseline) and with the joint distracted throughout the entire range of motion. The distance between the calculated location of the point of reference throughout the range of motion of the joint for both the baseline and distracted positions is representative of the laxity of the post-operative joint.

Figure 8:
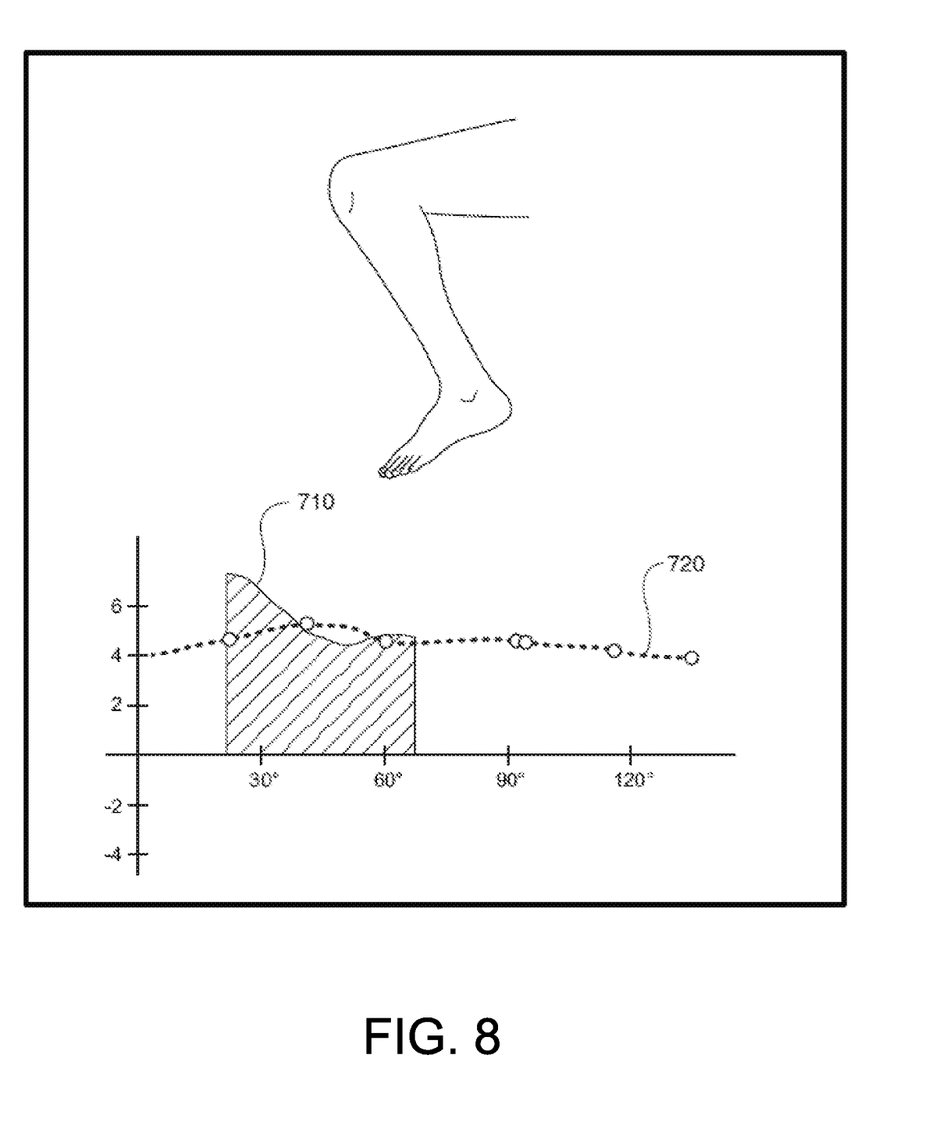
FIG. 8 depicts an illustration of a system display showing planned vs. post-operative laxity of a tracked joint through a range of motion, in accordance with certain embodiments of the invention.
Figure 9:
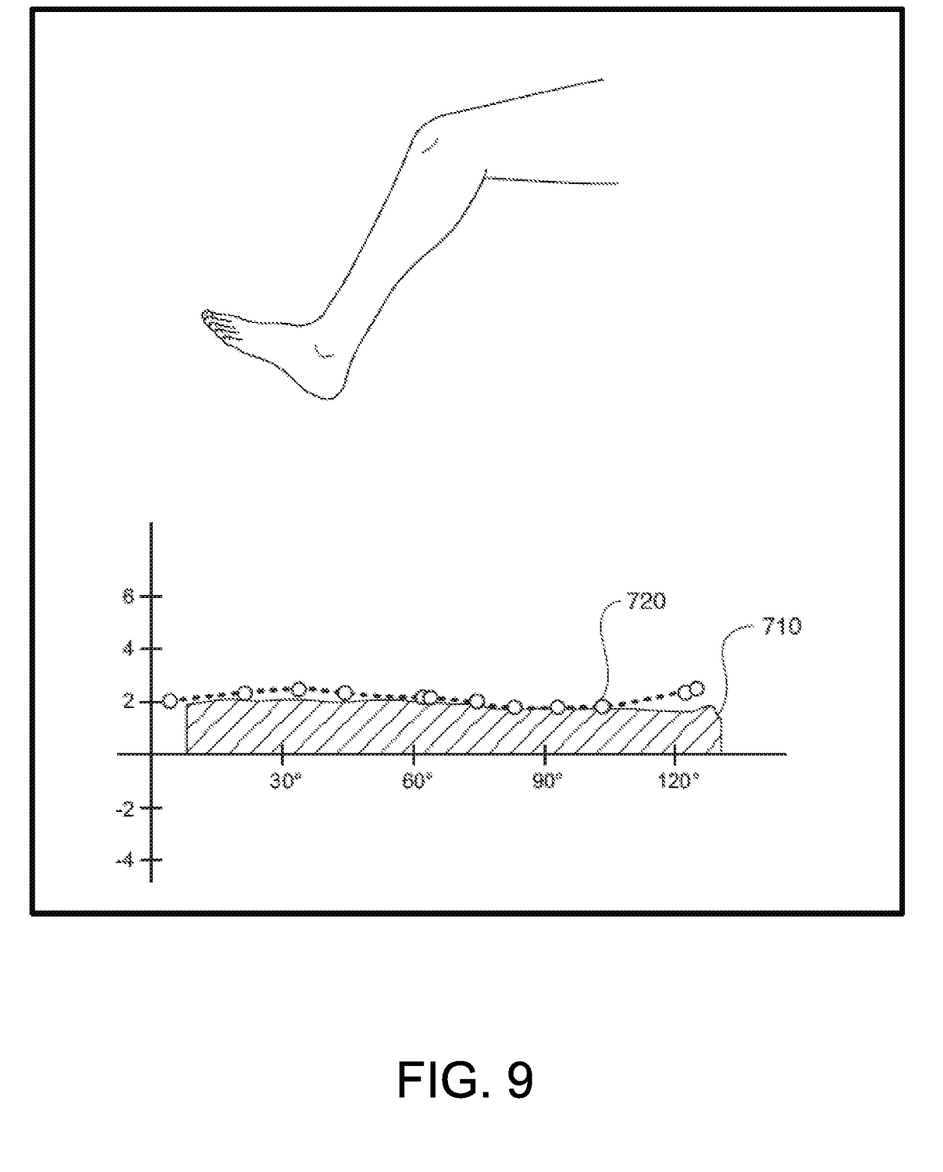
FIG. 9 depicts an illustration of a system display showing planned vs. post-operative laxity of a tracked joint through a range of motion, in accordance with certain embodiments of the invention.

Referring to FIGS. 8 and 9, the calculated laxity 710 in the post-operative joint is illustrated as the joint is moved through a range of motion. In certain implementations, the surgical team can be provided with a visual indication of whether the post-operative positions of the implants, and thus the postoperative laxity, matched the planned result. In certain embodiments, the goal is to end up with a post-operative laxity that is as close as possible to the laxity assumed or chosen in the surgical plan 720. In certain alternative embodiments, the post-operative laxity planned for in the surgical plan is based on statistical norms or other widely-accepted standard gaps for the joint in question.

Based upon the comparison of the calculated post-operative laxity 710 and the post-operative laxity assumption 720, the surgical plan can be altered or the surgeon can adjust the implant accordingly. For example, as shown in FIG. 8, the calculated post-operative laxity 710 can be plotted as a first laxity curve and the post-operative laxity assumption 720 can be plotted as a second laxity curve. By comparing the two laxity curves, one can determine whether the post-operative laxity is close to the laxity assumption. As shown in FIG. 8, the post-operative laxity 710 does not match the post-operative laxity assumption 720, thereby indicating that, for example, the patient is likely to experience movement issues with the joint implant. However, based upon the visual indication, the surgical plan can be updated and the surgeon can adjust one or more implant components. An updated results display, as shown in FIG. 9, can be displayed. In this example, the post-operative laxity 710 is closely aligned with the post-operative laxity assumption 720, thereby indicating that the patient is likely to have a similar or identical range of motion for the joint after the surgical procedure as they had prior to the surgical procedure.

Figure 10:
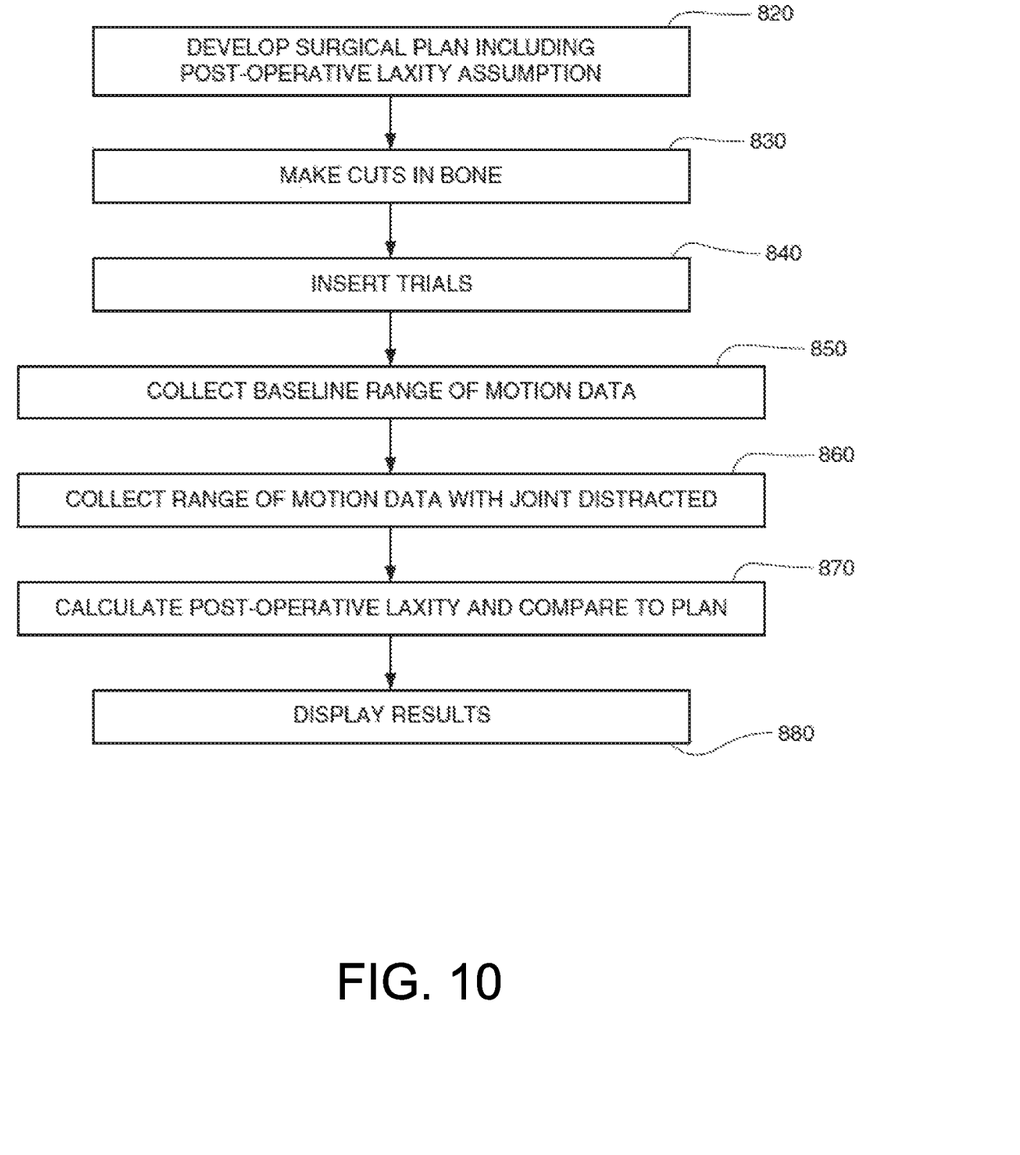
FIG. 10 depicts a flowchart illustrating the process of determining whether post-operative laxity is consistent with the surgical plan, in accordance with certain embodiments of the invention.

FIG. 10 illustrates a flowchart that summarizes certain embodiments of a method incorporating the techniques as described and taught in the present disclosure. For example, a surgical plan can be generated or developed 820 that incorporates, among other things, an assumed post-operative laxity in the joint to be replaced (e.g., post-operative laxity assumption 720 as described above). In certain embodiments, this post-operative laxity assumption can be a statistical average known in the art, while in other embodiments, the post-operative laxity assumption planned for in the surgical plan is based on the preference of the surgeon with knowledge of the patient. This assumed or planned—for laxity is used, along with at least implant sizing information, to develop 820 the surgical plan.

In certain implementation, the surgical plan can be used with a surgical system such as surgical system 100 as described above. For example, based upon instruction from the surgical system, the surgeon can make 830 one or more cuts in the bones of the operative joint in a manner consistent with the plan. In certain embodiments, this is performed with the assistance of the surgical system controlling a tracked cutting element.

Once the bones of the operative joint have been prepared, trial implants are inserted 840 into the prepared bone to test how well the plan was performed. To determine the post-operative laxity, the implants are pushed together, and the joint is moved throughout a full range of motion to obtain baseline data. The surgical system can be configured to collect 850 data related to the movement of the joint through the full range of motion when pressed together to determine a baseline data set. This baseline data is representative of the position of the bones where the implants are as close as possible to each other. In certain embodiments, such as UKR procedure, the lower extremity of the operative joint is pushed upward against the upper portion of the joint so that the implants are pressed against each other and the joint is put through its full range of motion.

Similarly, a perpendicular force can be applied to the lower extremity of the joint to generate maximum space in the operative portion of the joint, and the joint is again moved through a full range of motion. During this second or distracted movement, the surgical system can collect 860 distracted joint data. Based upon the collected distracted joint data, the surgical system can calculate 870 post-operative laxity information and compare this information to the surgical plan and the post-operative laxity assumption as described, for example, in the description of FIGS. 8 and 9 above.

It should be noted that application of a perpendicular force as described above is provided by way of example only. In certain implementations, the surgical procedure can be a UKR of the medial condyle. In such a case, the force is applied to the lower leg in a lateral direction (meaning the opposite of medial direction) so that the installed trial implants are moved as far away from each other as possible without damaging the ligaments.

Referring back to FIG. 8, the surgical system can be further configured to display 880 the laxity results. As noted above, the laxity results can include a display similar to those shown in FIG. 8 and above, comparing the post-operative laxity and the post-operative laxity assumption. In certain implementations, the laxity results can be incorporated into the surgical plan and displayed to enable the surgeon to quickly determine consistency of the post-operative joint with the surgical plan as well as make any changes to the surgical plan to adjust the laxity results.

It should be noted that, as discussed herein, the surgical plan can be created by and utilize one or more program modules. Generally, program modules include routines, programs, objects, components, data structures, etc., that perform particular tasks or implement particular abstract data types.

In certain embodiments, the surgical plan can be implemented by one or more computing devices such as computers, PCs, server computers configured to provide various types of services and/or data stores in accordance with aspects of the described subject matter. Components can be implemented by software, hardware, firmware or a combination thereof.

While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure as come within known or customary practice in the art to which these teachings pertain.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A system for determining bone laxity during a surgical procedure to replace at least a portion of a bone joint with an implant, the system comprising:
   a tracked probe comprising at least one probe marker, the tracked probe configured to provide an indication of at least one anatomical landmark on a bone during the surgical procedure; and
   a computer assisted surgical system comprising:
      a navigation system configured to track the tracked probe and at least one optical bone marker during the surgical procedure, and
      a processing device operably connected to the navigation system and a computer readable medium configured to store one or more instructions that, when executed, cause the processing device to:
         receive location information related to a position of the tracked probe and the at least one optical bone marker from the navigation system,
         pre-operatively generate a surgical plan comprising a post-operative laxity assumption based on one or more of standard gap information and statistical gap information,
         collect, after insertion of one or more trial components, first motion information related to movement of the joint through a first range of motion based on the position of the at least one optical bone marker,
         collect, after insertion of one or more trial components, second motion information related to movement of the joint through a second range of motion based on the position of the at least one optical bone marker,
         determine a post-operative laxity for the joint based on spatial differences in the position of the at least one optical bone marker between the first motion information and the second motion information,
         compare the post-operative laxity for the joint and the post-operative laxity assumption to determine laxity results for the surgical procedure,
         cause the laxity results to be displayed on a display operably connected to the processing device,
         modify the surgical plan based on input received from a user, and
         update the laxity results based on the modified surgical plan.

2. The system of claim 1, wherein the first motion information comprises baseline information collected while the joint is moved through the first range of motion wherein a first portion of the joint is touching a second portion of the joint.

3. The system of claim 2, wherein the first portion of the joint comprises a tibial implant and the second portion of the joint comprises a femoral implant.

4. The system of claim 2, wherein the second motion information comprises distracted motion information collected while the joint is moved through the second range of motion wherein the first portion of the joint is in a distracted position from the second portion of the joint.

5. The system of claim 1, wherein determining the laxity results comprises:
   plotting distance information associated with the post-operative laxity assumption to obtain a first laxity curve;
   plotting distance information associated with the post-operative laxity to obtain a second laxity curve; and
   comparing the first laxity curve and the second laxity curve.

6. The system of claim 1, wherein the computer readable medium is configured to store one or more additional instructions that, when executed, cause the processing device to update the surgical plan based upon the laxity results.

7. The system of claim 1, wherein the post-operative laxity assumption is based upon implant size information, preservation of an original joint line for the joint, and ensuring sufficient space in the joint for full range of motion.

8. The system of claim 7, wherein the sufficient space in the joint for full range of motion is determined based upon the standard gap information for the joint.

9. The system of claim 1, wherein the joint comprises a knee.

10. The system of claim 1, wherein the at least one bone marker comprises an optical navigation marker mounted on a patient's tibia.

11. A device for determining bone laxity during a surgical procedure to replace at least a portion of a bone joint with an implant, the device comprising:
   a processing device operably connected to a navigation system and a computer readable medium configured to store one or more instructions that, when executed, cause the processing device to:
      receive location information related to a position of a tracked probe and at least one optical bone marker from the navigation system,
      pre-operatively generate a surgical plan comprising a post-operative laxity assumption based on one or more of standard gap information and statistical gap information,
      track movement of the joint through a first range of motion and collect first motion information related to movement of the joint through the first range of motion based on the position of the at least one optical bone marker,
      track movement of the joint through a second range of motion and collect second motion information related to movement of the joint through the second range of motion based on the position of the at least one optical bone marker,
      determine a post-operative laxity for the joint based on spatial differences in the position of the at least one optical bone marker between the first motion information and the second motion information,
      compare the post-operative laxity for the joint and the post-operative laxity assumption to determine laxity results for the surgical procedure,
      cause the laxity results to be displayed on a display operably connected to the processing device,
      modify the surgical plan based on input received from a user, and
      update the laxity results based on the modified surgical plan.

12. The device of claim 11, wherein the first motion information comprises baseline information collected while the joint is moved through the first range of motion wherein a first portion of the joint is touching a second portion of the joint.

13. The device of claim 12, wherein the first portion of the joint comprises a tibial implant and the second portion of the joint comprises a femoral implant.

14. The device of claim 12, wherein the second motion information comprises distracted motion information collected while the joint is moved through the second range of motion wherein the first portion of the joint is in a distracted position from the second portion of the joint.

15. The device of claim 11, wherein determining the laxity results comprises:
   plotting distance information associated with the post-operative laxity assumption to obtain a first laxity curve;
   plotting distance information associated with the post-operative laxity to obtain a second laxity curve; and
   comparing the first laxity curve and the second laxity curve.

16. The device of claim 11, wherein the computer readable medium is configured to store one or more additional instructions that, when executed, cause the processing device to update the surgical plan based upon the laxity results.

17. The device of claim 11, wherein the post-operative laxity assumption is based upon implant size information, preservation of an original joint line for the joint, and ensuring sufficient space in the joint for full range of motion.

18. The device of claim 17, wherein the sufficient space in the joint for full range of motion is determined based upon the standard gap information for the joint.

19. The device of claim 11, wherein the joint comprises a knee.

20. The device of claim 11, wherein the at least one bone marker comprises an optical navigation marker mounted on a patient's tibia.

21. A method for using post-operative bone laxity measurements for aligning a cutting guide with respect to a target bone during a surgical procedure, the method comprising:
   collecting, after insertion of one or more trial components, motion information related to movement of a post-operative bone joint through a range of motion, wherein the motion information comprises a position of a first optical tracker on the target bone and a position of a second optical tracker on an adjacent bone, wherein the post-operative bone joint was operated on using a surgical plan comprising a post-operative laxity assumption determined pre-operatively based on one or more of standardized gap data and statistical gap data;
   determining a post-operative laxity for the post-operative bone joint based on the position of the first optical tracker and the position of the second optical tracker;
   comparing the post-operative laxity for the post-operative bone joint to the post-operative laxity assumption to determine laxity results for the surgical plan;
   generating a revised surgical plan based on the determined laxity results;

aligning the cutting guide with respect to the target bone using a computer assisted surgical system based on the revised surgical plan; and controlling a tracked cutting element by the computer assisted surgical system to complete one or more cuts to the target bone; and updating the determined laxity results after completing the one or more cuts.

22. The method of claim 21, wherein determining a post-operative laxity for the post-operative bone joint comprises comparing a relative position of the first optical tracker to the second optical tracker in each of a distracted state and a baseline state of the post-operative bone joint.

23. The method of claim 21, wherein the motion information further comprises a position of a reference point on one of the one or more trial components, wherein determining post-operative laxity for the post-operative bone joint comprises comparing a relative position of the reference point to one of the first optical tracker and the second optical tracker in each of a distracted state and a baseline state of the post-operative bone joint.

* * * * *